United States Patent [19]

Pomerantz et al.

[11] Patent Number: 5,139,338
[45] Date of Patent: Aug. 18, 1992

[54] METHOD AND APPARATUS FOR VOLUMETRIC DIGITIZATION OF 3-DIMENSIONAL OBJECTS

[75] Inventors: Itzchak Pomerantz, Kfar Sava; Barry Ben-Ezra, Ramat Hasharon; Gil Shamir, Raanana, all of Israel

[73] Assignee: Cubital Ltd., Herzlia, Israel

[21] Appl. No.: 433,657

[22] Filed: Nov. 8, 1989

[30] Foreign Application Priority Data

Nov. 10, 1988 [IL] Israel .................................. 88359

[51] Int. Cl.⁵ .......................... G01N 1/00; G01B 11/24
[52] U.S. Cl. ........................................ 356/376; 356/36
[58] Field of Search ................ 356/376–379, 356/382–385, 36; 354/76, 80, 81; 83/329, 330, 703; 264/40.12, 40.11, 40.15; 425/142; 364/474.01, 474.05

[56] References Cited

U.S. PATENT DOCUMENTS

| | | | |
|---|---|---|---|
| 3,649,108 | 3/1972 | Ahrens | 352/84 |
| 3,855,889 | 12/1974 | Wiley et al. | 83/329 |
| 3,884,563 | 5/1975 | Evans et al. | 356/36 |
| 4,272,049 | 6/1981 | Kindel | 264/40.1 |
| 4,404,684 | 9/1983 | Takada | 356/376 |
| 4,960,330 | 10/1990 | Kerschmann | 356/36 |

OTHER PUBLICATIONS

Prothero J. S. et al. "Three-dimensional reconstruction from serial sections: iv the reassembly problem" Computer & Biomed. Res (USA) vol. 19 No. 4 pp. 361–373 Aug. 1986.

Baker H. H. "Building, visualizing and computing on surfaces of evolution" IEEE Computer Graphics & Applications Jul. 1988, pp. 31–41.

Modern Plastics enclyclopedia. McGraw Hill 1988 p. 79.

R. T. Chin, "Survey-Automated Visual Inspection 1981–1987" Computer Vision, Graphics and Image Processing No. 41, pp. 346–381.

*Primary Examiner*—Davis L. Willis
*Assistant Examiner*—Hoa Pham
*Attorney, Agent, or Firm*—Ladad & Parry

[57] ABSTRACT

A system for volumetric digitization of three dimensional objects including apparatus for filling any cavities in a three dimensional object and volumes on the outside of the object with a generally opaque support material and solidifying the support material to a solid block having generally uniform hardness before digitizing is undertaken, apparatus for digitizing a first exposed surface of the object, apparatus operative following digitizing of the first exposed surface for removing a layer of predetermined thickness of the object to expose a second exposed surface and apparatus operative to digitize the second exposed surface of the object.

16 Claims, 10 Drawing Sheets

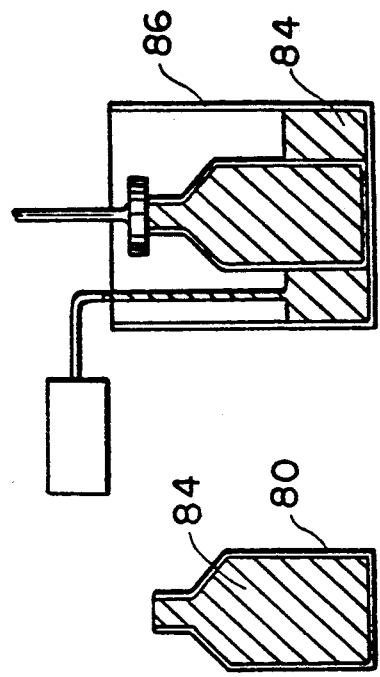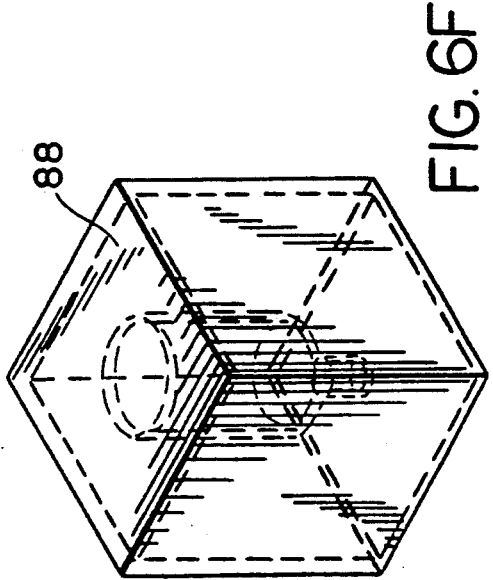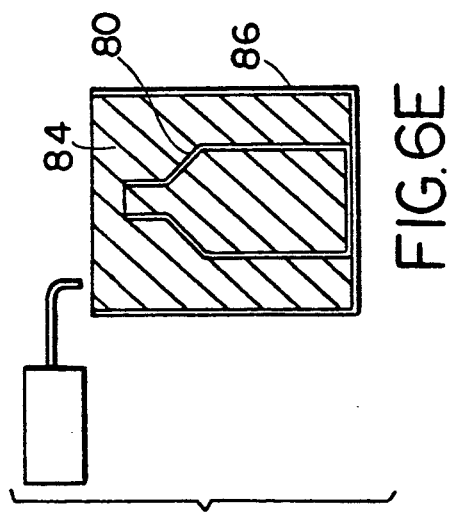

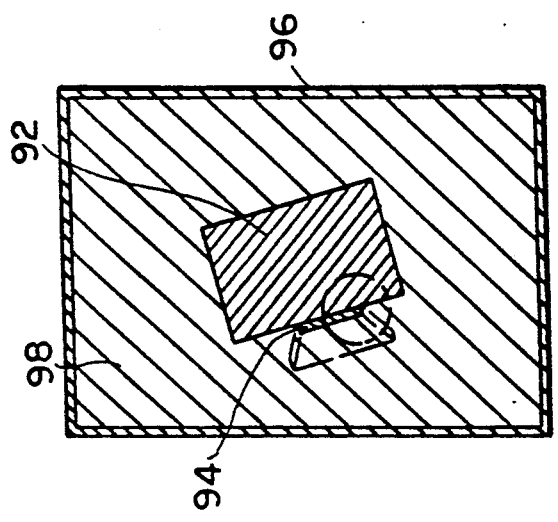
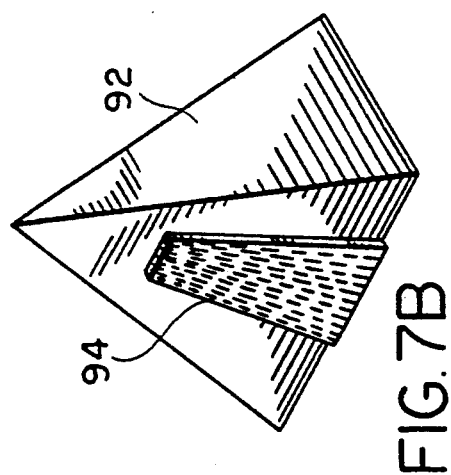
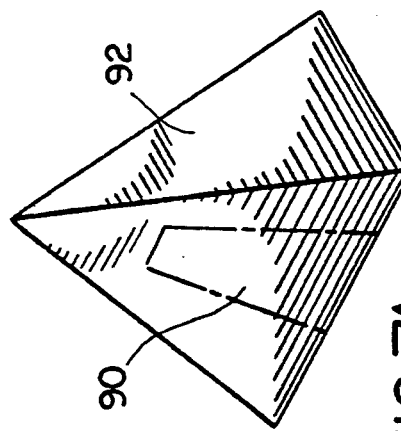
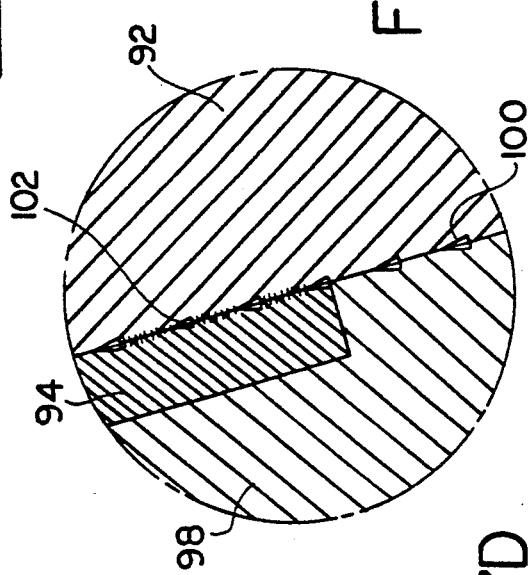
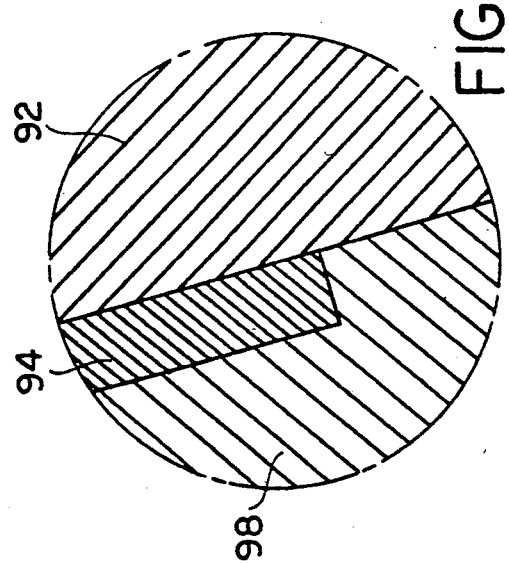

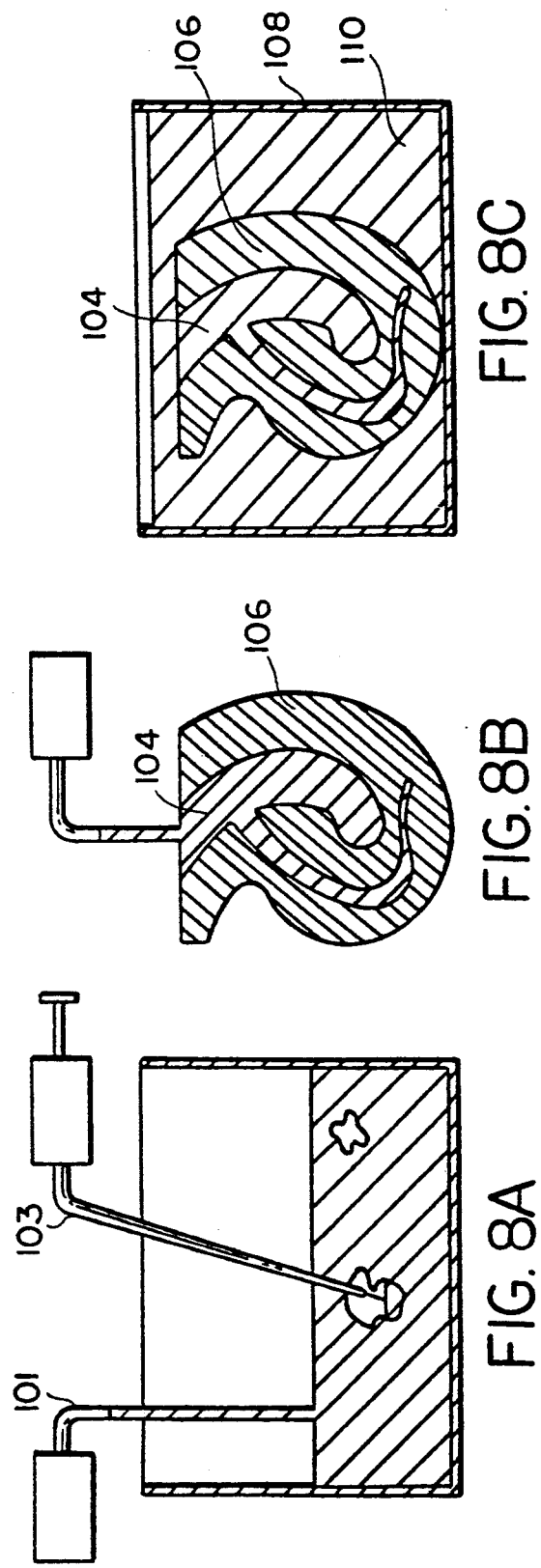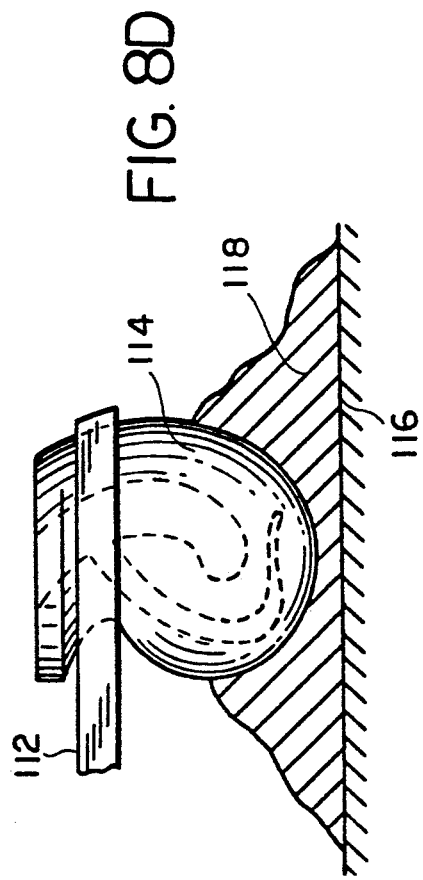

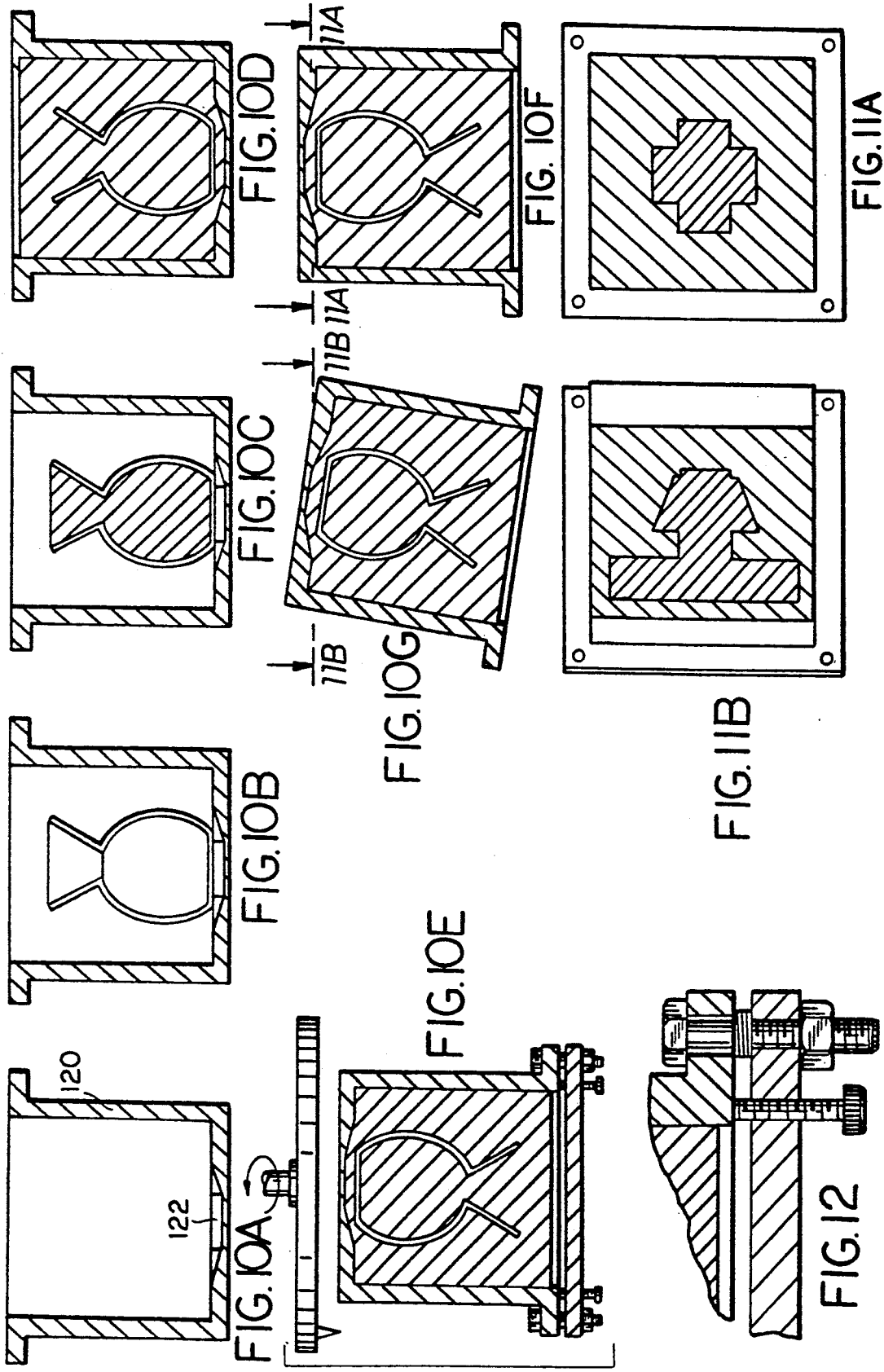

METHOD AND APPARATUS FOR VOLUMETRIC DIGITIZATION OF 3-DIMENSIONAL OBJECTS

FIELD OF THE INVENTION

The present invention relates to digitization of three-dimensional objects.

BACKGROUND OF THE INVENTION

The usefulness of digitization of three-dimensional objects is well established. There are known three dimensional digitizing devices which are operative to digitize only the exterior envelope. These include, for example, mechanical arms which follow the exterior face of an object, the coordinates of the tip of the arm being determined by shaft encoders in the joints of the arms. Another example of such digitizing devices employs a stylus which points to a location on the face of an object, while the coordinates of the tip of the stylus are determined by telemetry. A further example of such devices measures the reflection of a beam of energy, such as light, which is reflected off the exterior contours of an object.

A typical mechanical arm digitizer is described in *Digital Design,* April, 1984, page 104 and is indicated as being available from Micro Control of Vernon CT, U.S.A. under the designation 3D Digitizer.

A typical telemetric digitizer is known as 3-Space and is available from McDonnell Douglas of St. Louis, MO, U.S.A.

Apparatus for conversion of 3-dimensional points measured on a part surface into a CAD model is known as CADDInspector and is stated in the Klein Report, Vol. 10, No. 13, Jul. 13, 1988 as being available from CADKEY of Vernon, CT, U.S.A.

It is also known to generate three dimensional images of relatively soft tissues which are cut with a microtome. This technique does not provide registration of the images and is not suitable for engineering objects.

Computerized tomography and radiological scanners provide slice information for objects but generally are not suitable for use in an industrial environment in terms of their speed, model size capacity, accuracy, resolution and the types of materials on which they can operate.

In an article entitled "Three-dimensional reconstruction from serial sections: iv. The reassembly problem", by Prothero J. S. et al (*Computer, & Biomed. Res.* (USA), vol. 19, no. 4, pp. 361–373, August, 1986) there is described a reconstruction technique wherein thin slices are cut sequentially from an object. After cutting, the slices are digitized by conventional two-dimensional digitizing techniques.

In an article entitled "Building, visualizing and computing on surfaces of evolution", by H. Harlyn Baker (IEEE *Computer Graphics & Applications,* July, 1988, pp. 31–41) there is a discussion of reconstruction of three dimensional surfaces of an object from two dimensional slices thereof.

U.S. Pat. Nos. 3,649,108 and 3,884,563 both relate to layer-by-layer photographing of a specimen. After a given layer is photographed, that layer is removed from the specimen and discarded. U.S. Pat. No. 3,884,563 describes at column 2, line 15, the use of a computer scanner. U.S. Pat. No. 3,649,108 describes at column 3, lines 16–20, the use of a filler material which is usually translucent or transparent.

It may be fairly said that the prior art devices described above are not able to provide uniformly high resolution volumetric digitizing of generally all shapes of objects.

SUMMARY OF THE INVENTION

The present invention seeks to provide a highly accurate system for digitizing three dimensional objects.

There is thus provided in accordance with a preferred embodiment of the invention a system for volumetric digitization of three dimensional objects including apparatus for filling any cavities in a three dimensional object and volumes on the outside of the object with a generally opaque support material and solidifying the support material to a solid block having generally uniform hardness before digitizing is undertaken; apparatus for digitizing a first exposed surface of the object, apparatus operative following digitizing of the first exposed surface for removing a layer of predetermined thickness of the object to expose a second exposed surface and apparatus operative to digitize the second exposed surface of the object.

Further in accordance with an embodiment of the invention there is provided a system for volumetric digitization of three dimensional objects including apparatus for digitizing an exposed generally two-dimensional surface, apparatus for selective removal of a layer of predetermined thickness of an object to expose a generally two dimensional surface thereof, and control apparatus operative to cause the apparatus for digitizing to digitize a first exposed surface of the object, to cause the apparatus for selective removal to be operative following digitizing of the first exposed surface to remove a layer of predetermined thickness from the object to expose a second exposed surface and to cause the apparatus for digitizing to digitize the second exposed surface of the object.

Additionally in accordance with a preferred embodiment of the invention there is provided a method for digitizing a three dimensional object comprising the steps of: filling an cavities in a three dimensional object and volumes on the outside of the object with a generally opaque support material and solidifying the support material to a solid block having generally uniform hardness before digitizing is undertaken; digitizing a first exposed surface of the object, following digitizing of the first exposed surface removing a layer of predetermined thickness from the object to expose a second exposed surface and digitizing the second exposed surface of the object.

The operations of digitizing followed by removal of an additional layer to expose an additional surface and digitizing thereof normally continue until the entire volume of the object has been digitized.

In accordance with a preferred embodiment of the invention, any cavities in the three dimensional object and volumes on the outside of the object are filled with a support material and solidified to a solid block having generally uniform hardness before the digitizing process described above.

Additionally in accordance with a preferred embodiment of the invention, the removal of a layer of predetermined thickness of the object is effected by machining.

Further in accordance with a preferred embodiment of the present invention, the support material has a different color from that of the object, so as to provide contrast. Preferably, the support material is opaque so as to eliminate spurious readings due to light passing to the digitized surface from deeper layers.

Additionally in accordance with a preferred embodiment of the present invention, the two dimensional surface digitizations are merged into a three dimensional representation which may be in standard CAD format.

Further in accordance with a preferred embodiment of the invention, the digitization is carried out with a computerized automatic inspection system.

It is a particular feature of the present invention that the problem of registration between the various surface digitizations is obviated by carrying out the two dimensional digitization on intact surfaces of the solid block prior to their removal from the block rather than on surfaces of layers previously removed from the solid block.

BRIEF DESCRIPTION OF THE DRAWINGS

The present invention will be understood and appreciated more fully from the following detailed description, taken in conjunction with the drawings in which:

FIGS. 6A, 6B, 6C, 6D, 6E and 6F are illustrations of the steps in a solidification technique useful in the present invention;

FIGS. 7A, 7B, 7C, 7D and 7E are illustrations of differing levels of detail illustrating an aspect of the present invention;

FIGS. 8A, 8B, 8C and 8D are illustrations of four stages in a solidification technique useful in the present invention;

FIGS. 10A, 10B, 10C, 10D, 10E, 10F and 10G illustrate various stages in a solidification step employing the container of FIG. 9;

FIGS. 11A and 11B are sectional illustrations taken along the lines A—A and B—B of FIGS. 10F and 10G respectively; and FIG. 12 is an illustration of a detail of attachment of a cover onto the container of FIG. 9.

DETAILED DESCRIPTION OF PREFERRED EMBODIMENTS

Figure 1:
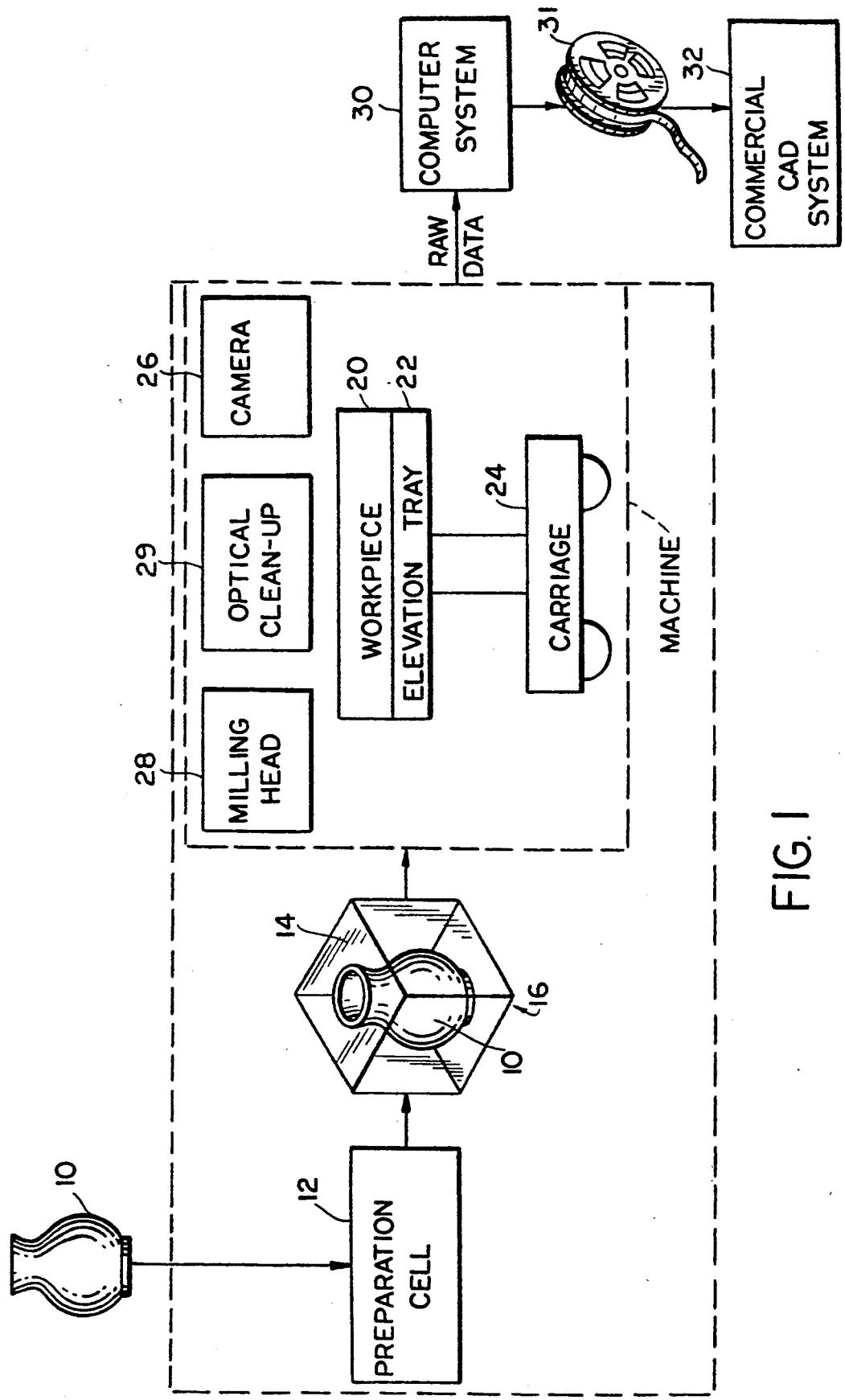
FIG. 1 is a generalized block diagram of a digitizing system constructed and operative in accordance with a preferred embodiment of the present invention.

Reference is now made to FIG. 1 which illustrates the basic principles of the present invention. An object 10, such as a vase, is initially subjected to what will here be termed a solidification procedure in a preparation cell 12. As will be described in greater detail hereinbelow, the internal cavity of the object 10 is filled with a filling material 14 and the volume outside of the object is filled to define a solid cube 16 or any other suitable shape, in which the object 10 is embedded.

Preferably the filling material 14 used to fill both the interior and the exterior of the object 10 in cube 16 is a material of hardness similar to that of the object 10. It is also desirable that the filling material be of a color different from the color of the object 10 and be opaque.

The cube 16 defines a workpiece, indicated by a reference number 20, which is supported on an elevation tray 22. Tray 22 is supported at a variable height on a carriage 24 which can move in the X - Y plane.

The workpiece 20 repeatedly and sequentially passes into and out of operative engagement with a camera 26, such as a CCD camera available from Audre, of Newport Beach, CA., for providing a 2-dimensional picture of a generally two dimensional surface thereof, a milling head 28, for removing a predetermined or selectable thickness from the object thereby to expose a new two-dimensional surface, and an optical clean up assembly 29, which prepares the newly exposed surface for the camera 26. The camera 26 may preferably form part of a computerized inspection system, such as a Vision-106 inspection system, commercially available from Optrotech Ltd. of Nes Ziona, Israel. An alternative commercially available system is a Model 1850 Automatic Optical Inspection System available from Gerber Scientific Instruments Co. of Hartford, CT.

The output of camera 26, in the form of raw data, preferably in digital raster form, is supplied to a computer system 30, such as an IBM PC, which prepares a computer aided design (CAD) output 31 in a conventional format for use by a conventional commercial CAD system 32, such as a Unigraphics system available from McDonnell Douglas Automation of St. Louis, Missouri, U.S.A. A review of algorithms and systems for such applications appears in "Survey - Automated Visual Inspection 1981-1987" by R. T. Chin, in *Computer Vision, Graphics and Image Processing*, No. 41, pp. 346-381, which is incorporated herein by reference.

The sequence of operation of the apparatus of FIG. 1 may be summarized as follows:

An object 10, or alternatively, more than one such object, which is to be volumetrically digitized in accordance with the present invention, is positioned in a suitable framing container defining the preparation cell 12 and is held in position, if necessary, by solid ribs, preferably made of a support material which is similar or identical to the support material used in the following step, when solidified.

Figure 4:
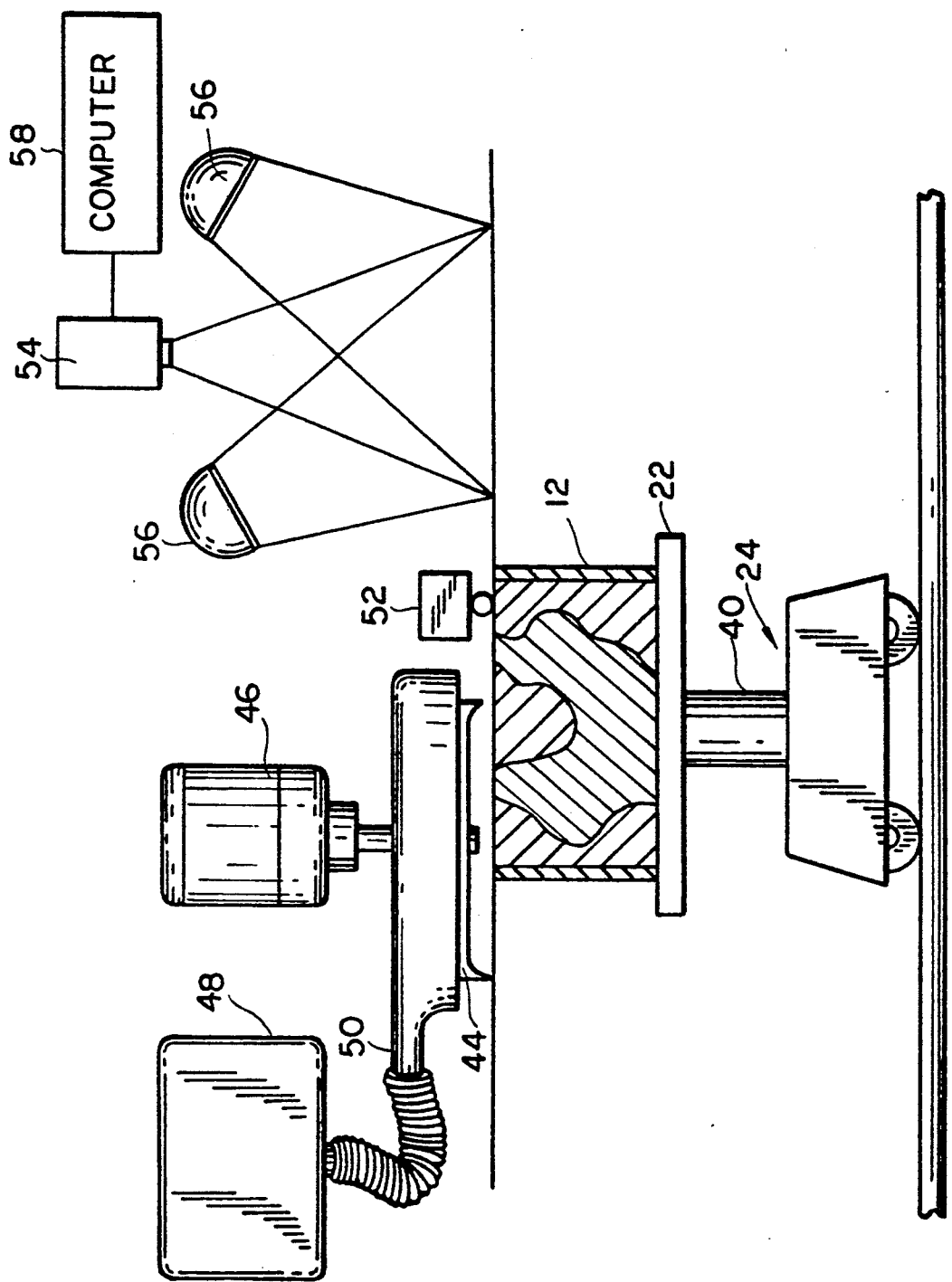
FIG. 4 is a pictorial illustration of part of the digitizing system of FIG. 1.

A solidifiable liquid support material 14, such as, for example, casting wax, polystyrene foam, gypsum or epoxy, is inserted into all of the cavities of the object and around the object so as to fill the interior volume of the preparation cell 12 (FIG. 1). Upon settling and solidification of the support material 14, a cube or other suitable volume 16 is defined, the contours of which correspond to those of preparation cell 12. At this point, volume 16 may be removed from cell 12. Alternatively, cell 12 may be dismantled. A further, preferred, alternative is to retain volume 16 within cell 12 as shown in FIG. 4.

The support material 14 has a number of important functions:

To support delicate parts of an object and to prevent distortion thereof as a result of milling;

To provide visual contrast between the object and the background so as to enable accurate imaging to be achieved;

To conceal parts of the object excluded from the exposed two dimensional layer from view, so as to preserve correctness of the imaging;

To enable tools and markers to be positioned as desired with respect to the object being digitized; and To enable multiple objects to be digitized in the same preparation cell at the same time.

The volume 16, defining workpiece 20, is then positioned on elevation tray 22 and such that the top of the workpiece is located at an operation level for operative engagement with the camera 26, milling head 28 and clean up unit 29.

An appropriate vertical resolution is selected. A typical resolution is 0.1 mm.

Operation is commenced by raising the tray by one resolution unit, typically 0.1 mm, and moving the tray across the milling head to remove a layer of thickness one resolution unit in thickness. The exposed layer is then treated by apparatus 29 to enhance the contrast between the object and the support material 14, as by wetting the exposed surface of the layer with a clear liquid, such as, for example, water or alcohol.

The exposed contrast-enhanced surface of the layer is scanned or photographed by camera 26 to produce a digital raster image.

The digital raster image is processed and the above steps are repeated until the entire object has been sliced at desired resolution and the layers thereof have been photographed.

The digital raster images of the various layers are combined and modified to produce a conventional CAD data- file output.

Figure 2:
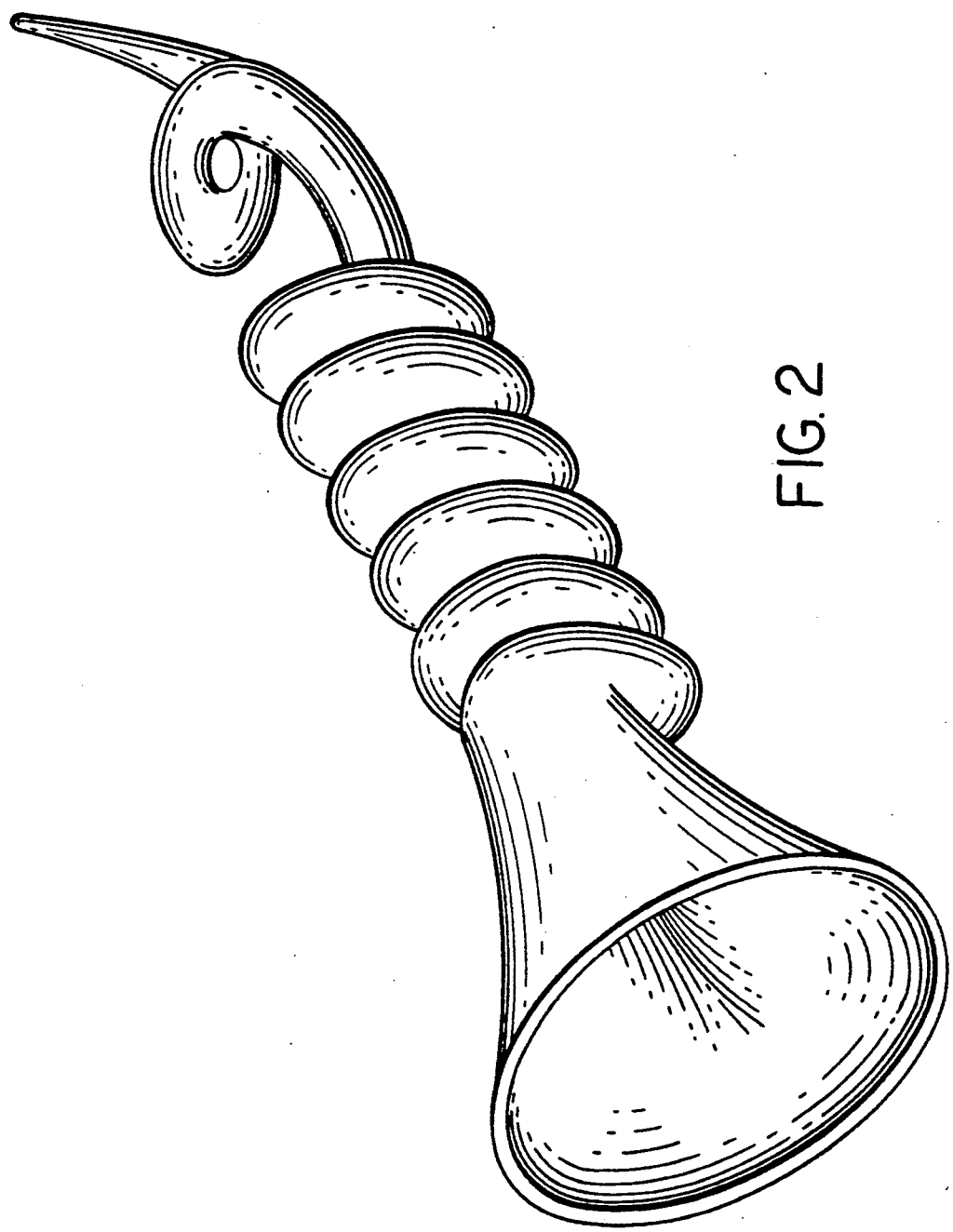
FIG. 2 is a pictorial image of an object that can be digitized using the system and techniques of the present invention.

FIG. 2 is a pictorial illustration of a relatively complex object which can be readily digitized in accordance with the present invention.

Figure 3A:
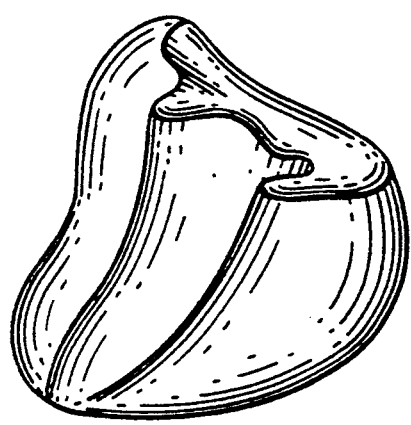
FIGS. 3A, 3B and 3C are illustrations of the slicing of an object.
Figure 3B:
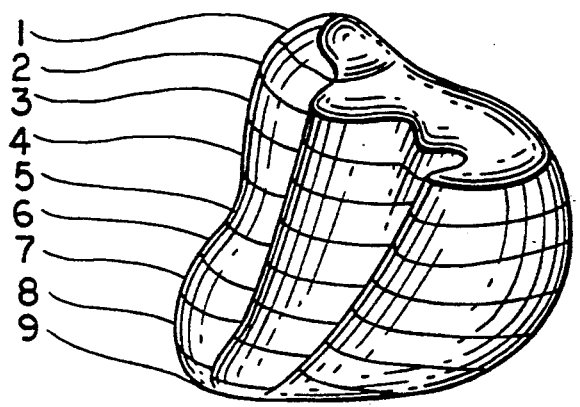
Figure 3C:
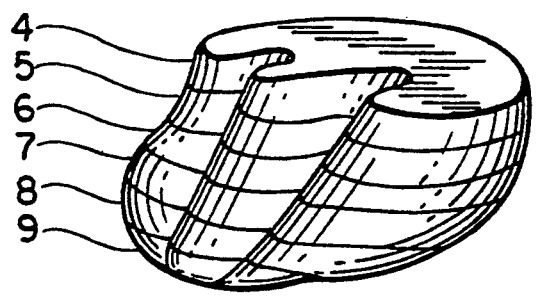

The slicing of a three-dimensional object can be readily visualized by considering FIGS. 3A-3C. FIG. 3A illustrates the object. FIG. 3B illustrates a layer pattern superimposed on the object and FIG. 3C illustrates the object with layers. 1-3 removed and layer 4 exposed.

It will be appreciated that the apparatus of the present invention may have a number of possible applications. These include, for example:

Digitization of three dimensional objects;

When combined with a suitable output device, generation of multiplied, scaled-up and/or scaled down versions of existing objects;

Testing casting molds and dies by digitizing a molded or cast product and comparing it to the design dimensions thereof;

Updating of a CAD file after a physical model has been physically modified by addition and/or subtraction of material; and Conversion of physical objects into standard CAD files compatible with commercially available CAD databases.

Reference is now made to FIG. 4 which is a pictorial schematic illustration of part of the apparatus shown in FIG. 1. The carriage 24 is shown to have a Z-axis elevation mechanism 40 which supports tray 22 onto which cube 16 is placed. It is noted that cube 16 may be enclosed by the preparation cell container 12 into which it was originally placed.

The milling head 28 (FIG. 1) typically comprises a fly cutter 44 of conventional design, such as is commercially available from Iscar Ltd. of Israel, driven by a motor 46 and associated with a vacuum cleaner 48 and dust trap 50 for dust control and collection.

The optical clean-up apparatus 29 typically comprises a wet rotating brush or a line of spraying sprinklers 52, while camera 26 (FIG. 1) typically comprises a digital video camera 54 associated with illumination apparatus 56 and a control computer 58, such as in the above-mentioned Vision 106 inspection system manufactured by Optrotech Ltd.

Figure 5A:
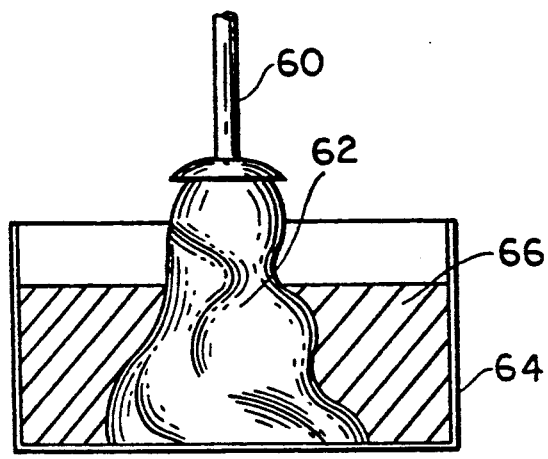
FIGS. 5A and 5B are pictorial illustrations of two different techniques for holing an object in a desired position during solidification of the support material.

It will be appreciated that the orientation of the object 10 in the preparation cell 12 determines the coordinates that the system will assign to it prior to an coordinate modification. FIG. 5A illustrates the use of a piston 60 to force an object 62 to the bottom of a preparation cell 64, filled with a support material 66, such that the flat bottom of the object 62 lies along the flat bottom of the preparation cell 64.

Figure 5B:
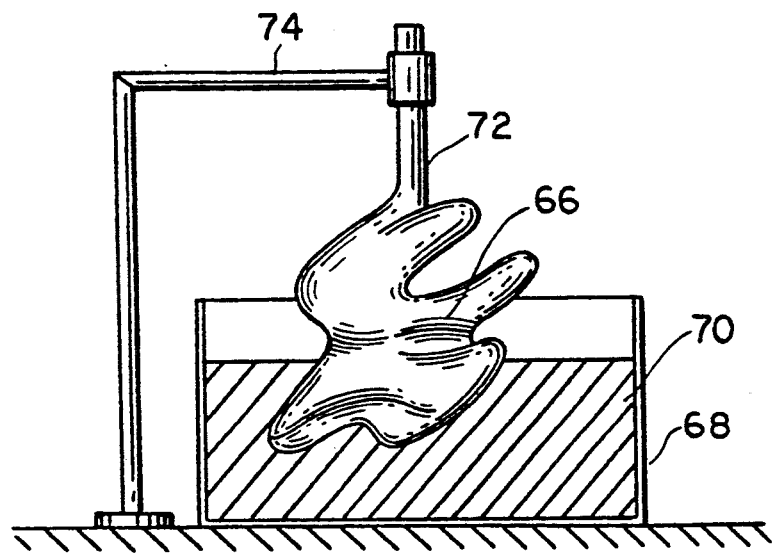

FIG. 5B illustrates suspension of an object 66 in a preparation cell 68 filled with a support material 70. Preferably the object 66 has attached thereto a support rod 72 formed of solidified support material 70. The rod 72 is, in turn, held in place by means of a support member 74.

Figure 9:
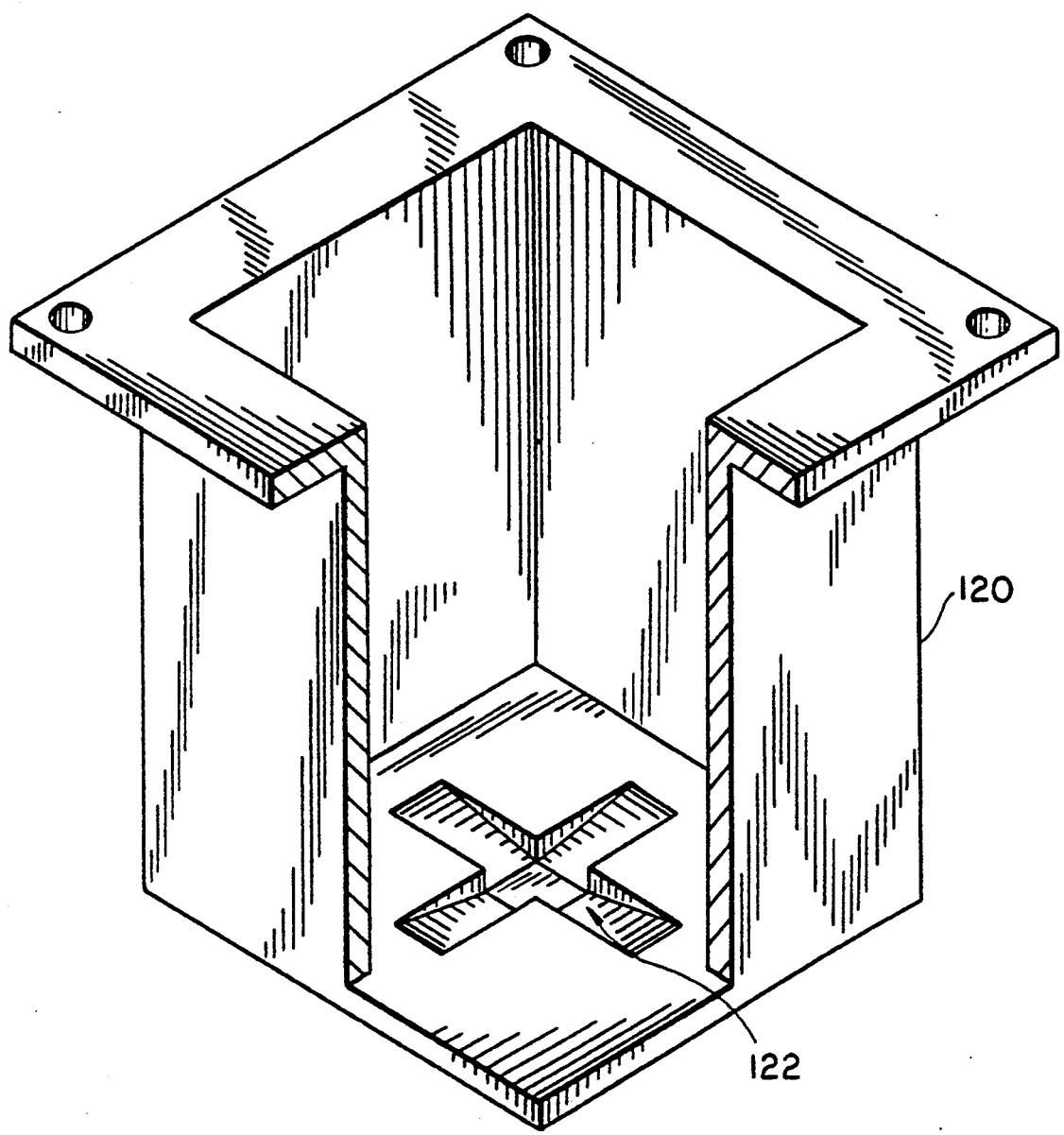
FIG. 9 is a pictorial illustration of a solidification container having a molded reference indication.

Reference is now made to FIGS. 6A-6F, which illustrate the various stages of preparing an object having an internal cavity for digitization in accordance with the present invention. A typical object 80 having an internal cavity 82 is shown in FIG. 6A. The internal cavity 82 is filled with support material 84 as shown in FIG. 6B, the filled object being seen in FIG. 6C. The object is then placed in a preparation cell 86 and the volume outside of the object 80 is then filled with support material, the filled preparation cell being shown in FIG. 6E. The solidified cube 88 is shown in FIG. 6F and is seen upside down, for example, which may be a preferred orientation for digitization, particularly when a preparation cell of the type illustrated in FIG. 9 is employed or when it is desired to avoid milling of support material overlying an object. The cube 88 may be machined together with the preparation cell 86 or after removal therefrom.

As noted above various tools or reference indicators may be digitized together with an object. This may be desirable when it is desired to instruct a computer to make certain changes in the object being digitized at given locations which can be indicated by markers. The markers may also be used to indicate possible separations between CAD files or portions of a CAD file.

FIG. 7A illustrates an area 90 on an object 92, which it is desired to mark. In FIG. 7B, the area 90 is covered by a relatively thick layer of paint 94 or other marking substance. FIG. 7C illustrates a typical section of the marked object of FIG. 7B located in a preparation cell 96, filled with a support material 98.

FIG. 7D illustrates, in enlargement, the circle appearing in FIG. 7C. It is noted that there are defined three different color to color interfaces; between the object 92 and the marking material 94, between the marking material 94 and the support material 98 and between the object 92 and the support material 98. Standard edge detection software which is employed in the Optrotech Vision 106 system described above may be employed for vectorizing each of the above interfaces.

FIG. 7E depicts an illustration of the results of vectorization, two different lists of vectors 100 and 102 being defined along the interfaces between the object 92 and the support material 98 and the marking material 94 respectively. It is noted that the interface between the marking material 94 and the support material 98 is ignored as not being of interest. It is appreciated that if the two different lists of vectors are accumulated from layer to layer, they define separate surfaces as desired for marking.

Some preferred materials for use as support materials are listed below:

Casting wax, such as type 999 available from Argueso of Mamaroneck, New York, U.S.A.

Polystyrene foam, such as that described at page 79 of Modern Plastics Encyclopedia, McGraw Hill, 1988 (incorporated herein by reference).

Epoxy, such as casting epoxy type 3142-66E available from Delta Chemicals, of Ramat Gan, Israel Gypsum FIGS. 8A-8D illustrate various techniques for inserting support materials into and around an object to be digitized. In view one, pouring is indicated at reference numeral 101, while injecting is illustrated at reference numeral 103. Internal cavities 104 in an object 106 may be prefilled outside of a preparation cell as shown in FIG. 8B. The prefilled object 106 may then be placed in a preparation cell 108 for further filling of support material 110, as shown in FIG. 8C. This two stage filling technique may be particularly useful when a more direct technique might produce air bubbles.

According to another alternative a solid base 112 may be cast onto an object 114, outside a preparation cell, for use in precise orientation of the object with respect to a given surface 116, as by solidified support material 118.

According to an alternative embodiment of the invention, the object may be coated by any desired technique, such as dipping and spraying.

Reference is now made to FIG. 9, which illustrates a preparation cell 120, defining at its bottom a patterned recess 122, which, when machined, provides a two-dimensional pattern indicating the error in orientation of the preparation cell 120 with respect to the coordinate system of the digitizing system. Accordingly the carriage 24 and tray 22 (FIG. 1) may have apparatus for adjustment of the positions thereof in accordance with the measured error in position of the preparation cell 120, prior to digitization.

The particular recess configuration illustrated in FIG. 9 has a number of advantages:

a. It separates the error into X and Y components.

b. It becomes more "sensitive" as machining continues therethrough towards the object to be digitized.

FIGS. 10A-10D illustrate the various steps of preparing an object for digitization using a preparation cell 120 of the type shown in FIG. 9, having a reference recess 122. As seen in FIG. 10B, an object 130 is placed on the floor of the preparation cell 120 above the recess 122. The object is filled with a support material 132 as seen in FIG. 10C and then the remainder of the preparation cell 120 is filled as seen in FIG. 10D.

Following solidification of the support material 132, the preparation cell is turned upside down and is mounted on an adjustable support assembly 134 for machining, as by a fly cutter 136, as shown in FIG. 10E. FIG. 10F shows the preparation cell 120 in a generally level orientation and FIG. 10G shows the preparation cell in a non-level orientation. FIGS. 11A and 11B illustrate the appearance of the recess 122 when initial layers are taken. It may appreciated that from the appearance of the recess 122, the degree of levelness can be determined and suitable adjustments can be made. FIG. 12 illustrates a detail of base assembly 134 including a spring loaded mounting screw 140 for adjustment of the orientation of the preparation cell 120 on base 134 to achieve desired leveling thereof.

It will be appreciated by persons skilled in the art that the present invention is not limited to what has been particularly shown and described hereinabove. Rather, the scope of the present invention is defined only by the claims which follow:

We claim:

1. A system for volumetric digitization of a three-dimensional object having cavities, the system comprising:

means for filling said cavities in the three-dimensional object and volumes on the outside of the object with a generally opaque support material, said support material, when solidified having generally the same hardness as that of said object and solidifying said support material to a solid block having generally uniform hardness before digitizing is undertaken;

means for digitizing a first exposed surface of the object;

machining means including a fly cutter, operative following digitizing of the first exposed surface for removing a layer of predetermined thickness from the object, without substantially distorting the remainder of the object, to expose a second exposed surface of the object; and means for digitizing the second exposed surface of the object.

2. A system according to claim 1 and wherein the color of said support material differs from that of the object, thereby to provide contrast.

3. A system according to claim 1 also comprising means for merging a plurality of two dimensional surface digitizations into a three dimensional representation.

4. A system for volumetric digitization of three-dimensional objects having cavities, said system comprising:

means for filling said cavities in a three-dimensional object and volumes on the outside of the object with a generally opaque support material, said support material, when solidified having generally the same hardness as that of said object and solidifying said support material to a solid block having generally uniform hardness before digitizing is undertaken;

means for digitizing an exposed generally two-dimensional surface of an object;

machining means including a fly cutter for selective removal of a layer of predetermined thickness from an object, to expose a generally two-dimensional surface thereof; and control means operative to cause the means for digitizing to digitize a first exposed surface of the object, to cause the means for selective removal to be operative following digitizing of the first exposed surface to remove a layer of predetermined thickness of the object to expose a second exposed surface and to cause the means for digitizing to digitize the second exposed surface of the object.

5. A system according to claim 4 and wherein the color of said support material differs from that of the object, thereby to provide contrast.

6. A system according to claim 4 also comprising means for merging a plurality of two dimensional surface digitizations into a three dimensional representation.

7. A method according to claim 6 and wherein said three dimensional representation is a CAD representation.

8. A method for digitizing a three-dimensional object including cavities, the method comprising the steps of:
    filling said cavities in the three-dimensional object and volumes on the outside of the object with generally opaque support material, said support material, when solidified having generally the same hardness as that of said object and solidifying said support material to a solid block having generally uniform hardness before digitizing is undertaken;
    digitizing a first exposed surface of the object;
    following digitizing of the first exposed surface machining, using a fly cutter, a layer of predetermined thickness from the object to provide a second exposed surface of the object; and
    digitizing the second exposed surface of the object.

9. A method according to claim 8 and wherein the steps of digitizing a surface followed by machining of an additional layer to expose an additional surface and digitizing of the additional surface continue until the entire volume of the object has been digitized.

10. A method according to claim 9 and wherein the color of said support material differs from that of the object, thereby to provide contrast.

11. A method according to claim 9 and also comprising the step of merging a plurality of two dimensional surface digitizations into a three dimensional representation.

12. A method according to claim 8 and wherein the color of said support material differs from that of the object, thereby to provide contrast.

13. A method according to claim 8 and also comprising the step of merging a plurality of two dimensional surface digitizations into a three dimensional representation.

14. A system according to claim 13 and wherein said three dimensional representation is a CAD representation.

15. A system for volumetric digitization of a hollow three-dimensional object comprising:
    means for filling with a material, which when harened, has generally the same hardness as that of said object and solidifying a hollow three dimensional object to a solid block having generally uniform hardness before digitizing is undertaken;
    means for digitizing a first exposed surface of the object;
    fly cutter means operative following digitizing of the first exposed surface for removing a layer of predetermined thickness of the object, without substantially distorting the remainder of the object, to expose a second exposed surface of the object; and
    means for digitizing the second exposed surface of the object.

16. A method for digitizing a hollow three-dimensional object comprising the steps of:
    filling said hollow three-dimensional object with a material, which when harened, has generally the same hardness as that of said object;
    solidifying said hollow three dimensional object in a solid block having generally uniform hardness before digitizing is undertaken;
    digitizing a first exposed surface of the object;
    following digitizing of the first exposed surface fly cutting a layer of predetermined thickness from the object to provide a second exposed surface of the object; and
    digitizing the second exposed surface of the object.

* * * * *